United States Patent [19]

Iovine et al.

[11] Patent Number: 4,596,850
[45] Date of Patent: Jun. 24, 1986

[54] IMIDAZOLIDINONE POLYMERS USEFUL AS NONWOVEN BINDERS

[75] Inventors: Carmine P. Iovine, Bridgewater; Joseph G. Palmer, Rocky Hill; James L. Walker, Whitehouse Station, all of N.J.

[73] Assignee: National Starch and Chemical Corporation, Bridgewater, N.J.

[21] Appl. No.: 682,650

[22] Filed: Dec. 17, 1984

Related U.S. Application Data

[62] Division of Ser. No. 473,922, Mar. 15, 1983, abandoned.

[51] Int. Cl.$^4$ .......................................... C08F 226/06
[52] U.S. Cl. .................................... 524/548; 526/263
[58] Field of Search ......................... 526/263; 524/548

[56] References Cited

U.S. PATENT DOCUMENTS

| | | | |
|---|---|---|---|
| 2,828,224 | 3/1958 | Alps et al. ............................ | 524/548 |
| 2,883,304 | 4/1959 | Kine et al. ............................ | 524/548 |
| 3,112,156 | 11/1963 | Vail et al. ............................ | 8/116.3 |
| 3,260,565 | 7/1966 | Beachem ............................ | 8/116.3 |
| 3,304,312 | 2/1967 | Beachem ............................ | 260/309.7 |
| 3,356,654 | 12/1967 | Sekmakas ............................ | 260/78.5 |
| 4,104,220 | 8/1978 | Sims ................................... | 524/548 |

FOREIGN PATENT DOCUMENTS

| | | |
|---|---|---|
| 1172265 | 6/1964 | Fed. Rep. of Germany . |
| 1171437 | 6/1964 | Fed. Rep. of Germany . |
| 1171438 | 6/1964 | Fed. Rep. of Germany . |
| 1959919 | 2/1971 | Fed. Rep. of Germany . |
| 2535598 | 2/1977 | Fed. Rep. of Germany . |
| 1557277 | 12/1979 | United Kingdom . |

OTHER PUBLICATIONS

S. L. Vail et al., "4,5-Dihydroxy-2-Imidazolidinone System for Crosslinking Cotton" Text. Res. J. 1969 39 (1), 86–93 C.A. 70 79030m.

*Primary Examiner*—Harry Wong, Jr.
*Attorney, Agent, or Firm*—Margaret B. Kelley; Edwin M. Szala

[57] ABSTRACT

Novel polymerizable imidazolidinone monomers, useful in the preparation of self-crosslinking polymers, have the general structure

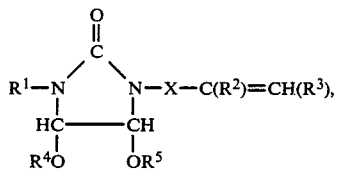

wherein $R^1$ is H or a $C_1$–$C_6$ linear or branched alkyl or hydroxyalkyl group; X is a divalent radical selected from the group consisting of

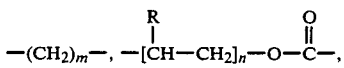

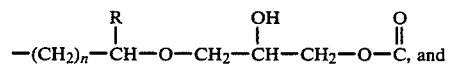

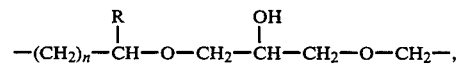

with R being H or $CH_3$, m being 0–5, and n being 1–5; $R^2$ is H or $CH_3$; $R^3$ is H or

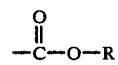

with R' as defined above; and $R^4$ and $R^5$ are independently H or linear or branched $C_1$–$C_4$ alkyl groups. In a preferred embodiment, aqueous emulsions of the imidazolidinone-containing polymers (e.g. 45–60% vinyl acetate, 34–52% butyl acrylate, and 3–6% imidazolidinone) and an acid-curing catalyst (e.g. $ZnCl_2$) are used as formaldehyde-free binders for nonwoven textiles.

20 Claims, No Drawings

IMIDAZOLIDINONE POLYMERS USEFUL AS NONWOVEN BINDERS

This application is a division of application Ser. No. 473,922, filed Mar. 10, 1983, now abandoned.

BACKGROUND OF THE INVENTION

This invention relates to novel polymerizable imidazolidinone monomers, their preparation, and their use to form self-crosslinking polymers which are thermosettable without the release of formaldehyde. It also relates to the use of such polymers in emulsion form as nonwoven binders.

It is well-known in the art to employ self-crosslinking polymers, either in emulsion or solution form, as coatings, binders, or adhesives for a variety of substrates. Self-crosslinking polymers are distinguished from crosslinkable polymers in that the latter contain a functionality, such as a carboxyl group, which can only be crosslinked by the addition of a co-reactant (i.e., crosslinker) to the polymer emulsion or solution. A typical crosslinkable system can be represented as follows:

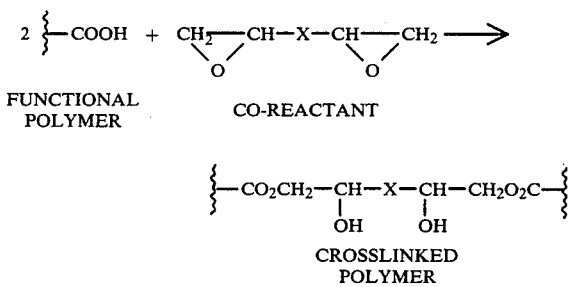

FUNCTIONAL POLYMER   CO-REACTANT

CROSSLINKED POLYMER

In contrast, self-crosslinking polymers contain a functionality which is self-reactive and consequently do not require the use of a co-reactant species per se. A typical self-crosslinking system can be represented as follows:

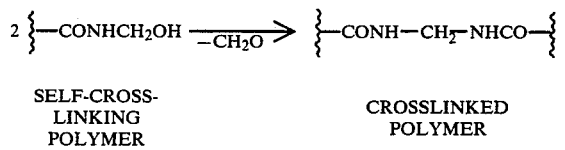

SELF-CROSS-LINKING POLYMER   CROSSLINKED POLYMER

The advantages of the self-crosslinking polymer systems are their simplicity, economy, and particularly their efficiency. Such systems have been used as textile adhesives, non-woven binders, pigment binders for glass fabrics, and fabric finishing agents for hand and weight modification. On curing, such systems produce textile products with excellent durability to washing and dry cleaning. They have also been used in pigment printing and dyeing and as a binder for paper.

Both the self-crosslinking and crosslinkable polymer systems of the prior art suffer from the disadvantage that toxic free formaldehyde is present either during the curing or the preparation of the polymers. The self-crosslinking systems, which are typically formaldehyde-amide polymeric adducts containing methylolacrylamide repeating units, liberate formaldehyde during curing of the crosslinked thermoset polymer. The crosslinkable systems, which are typically based on urea-formaldehyde or melamine-formaldehyde resins and crosslinkers, may contain residual free formaldehyde.

In addition to the odor problems created by the presence of free formaldehyde, the dermatitic effect is a serious problem. The exposure of operating personnel and consumers to formaldehyde has been a recent concern of both industry and regulatory agencies. This has lead to the search for formaldehyde-free systems, especially self-crosslinking, formaldehyde-free systems for use as nonwoven binders.

SUMMARY OF THE INVENTION

The present invention provides, as a composition of matter, an imidazolidinone of the general structure:

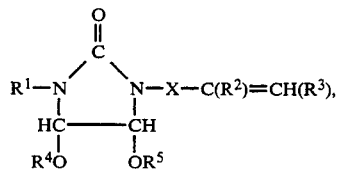

wherein $R^1$ is hydrogen or a $C_1$-$C_6$ linear or branched alkyl group; X is a divalent radical selected from the group consisting of

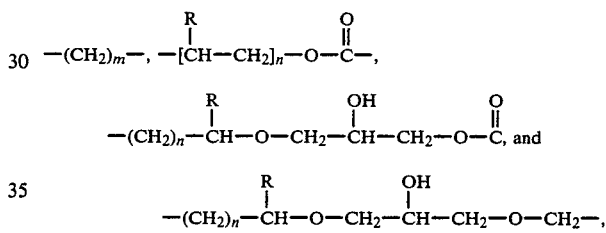

with R being hydrogen or a methyl group, with m being an integer from 0 to 5, and with n being an integer from 1 to 5, preferably m or n being 1; $R^2$ is hydrogen or a methyl group; $R^3$ is hydrogen or a

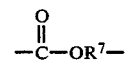

group with $R^7$ being hydrogen or a linear or branched $C_1$-$C_6$ alkyl or hydroxyalkyl; and $R^4$ and $R^5$ are independently hydrogen or a linear or branched $C_1$-$C_4$ alkyl group.

It also provides homopolymers and polymers thereof with monomer(s) containing at least one ethylenically unsaturated group.

In a preferred embodiment it provides emulsion (latex) polymers containing about 1–15%, preferably 3–6%, by weight of the above monomers and about 85–99%, preferably 94–97%, of an ethylenically unsaturated monomer, such as ethylene, vinyl acetate, ethyl acrylate, butyl acrylate, methyl methacrylate and the like, for use as formaldehyde-free binders for nonwoven textiles. A typical polymer contains about 45–60% vinyl acetate, 34–52% butyl acrylate, and about 3–6% of the self-crosslinking imidazolidinone.

DESCRIPTION OF THE PREFERRED EMBODIMENTS

The novel monomers herein are typically prepared by reacting an ethylenically unsaturated urea derivative with glyoxal. The urea derivatives are usually well known compounds previously reported in the chemical literature. Methods for their preparation are described in Synthetic Organic Chemistry by R. B. Wagner and H. D. Zook, John Wiley & Sons, 1963, p. 645. Two suitable methods include the reaction of isocyanates with amines, i.e.

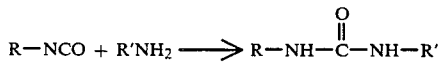

wherein R or R' may be an unsaturated group, and the reaction of amines with urea, i.e.

wherein R" is an unsaturated group.

In the typical isocyanate reaction, the isocyanate compound is dissolved in an aprotic dry solvent such as toluene at about 40% concentration. The entire reaction system is protected from moisture by suitable drying tubes, inert gas purge, or the like. The amine is slowly added to the solution at a temperature not exceeding 10°–15° C. In the case of ammonia or simple alkyl amines, this component is a gas and it is bubbled subsurface. The reaction is exothermic and adequate cooling may be required. The urea derivative usually precipitates as it forms and may be recovered from the reaction mixture by filtration. The derivative is then washed and dried.

In the typical amine reaction, the amine and urea are combined and heated at 120°–150° C. with the evolution of ammonia. When the reaction mixture reaches the required weight, the heating is stopped and the solid mass is recrystallized to recover the urea derivative.

In the imidazolidinone preparation, the urea compound is dissolved in sufficient water and gloxal to provide a solution of about 50% theoretical solids (based on imidazolidinone being prepared). The glyoxal reagent, used in stoichiometric amounts, may vary in form (e.g. 40% aqueous solution, 80% powder, p-dioxane diol, or the like). The pH of the mixture is adjusted to 7–7.5 with sodium hydroxide. Heat is applied to raise the temperature of the mixture to 45°–80° C. to effect complete reaction. The reaction is monitored by titrating for glyoxal content. When the reaction is complete, the monomer solution is generally diluted to 40% solids by the addition of water and the diluted mixture treated with activated charcoal. When the hydroxyl groups of the imidazolidinone ring are substituted with alkyl groups, suitable starting materials for the imidozolidinones may be prepared using well-known methods described in Synthesis 243 (1973a).

The above imidazolidinone monomers are useful as vinyl polymerizable monomers (i.e. monomers polymerizable by vinyl type polymerization procedures). They may be used to form homopolymers or their mixtures may be used to form polymers thereof. They may also be used to form addition polymers with other ethylenically unsaturated monomers. The polymers may be prepared by solution, emulsion, precipitation, suspension, or bulk polymerization techniques. The preferred method is emulsion polymerization.

Suitable comonomers include one or more monomers containing at least one ethylenically unsaturated group such as (meth)acrylonitrile; (meth)acrylic acid and the esters, amides and salts thereof; itaconic acid and its functional derivatives, preferably the esters; maleic anhydride; maleic and fumaric acids and the esters thereof; vinyl ethers and esters; styrene; ethylene; vinyl and vinylidene chlorides; and the like.

The preferred addition polymers for use as formaldehyde-free binders for non-woven textiles are polymers containing about 1–15%, preferably 3–5%, by weight of the above imidazolidinone monomers and about 99–85%, preferably 97–95%, by weight of one or more ethylenically unsaturated monomers such as ethylene, vinyl acetate, ethyl acrylate, butyl acrylate, or methyl methacrylate. The preferred imidazolidinone monomers for this use include 3-(methacryloxyethyl)-4,5-dihydroxy-2-imidazolidinone, 1-ethyl-3-allyl-4,5-dihydroxy-2-imidazolidinone, and 3-allyl-4,5-dihydroxy-2-imidazolidinone.

The following examples will more fully illustrate the embodiments of this invention. In the examples, all parts and percentages are given by weight and all temperatures are in degrees Celsius unless otherwise noted.

EXAMPLE I

This example describes the preparation of the 3-(methacryloxyethyl)-4,5-dihydroxy-2-imidazolidinone (MEDHEU). The two-step reaction sequence was as follow:

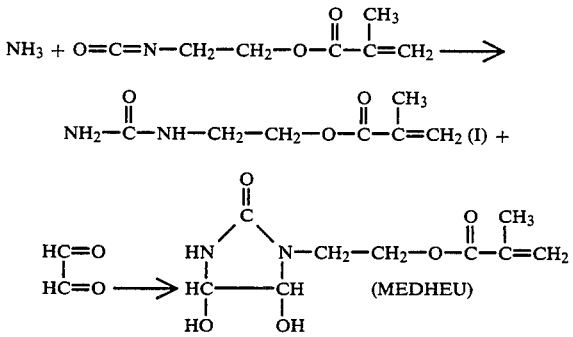

A three liter round bottom flask equipped with a thermometer, agitator, condenser, drying tube and a gas inlet tube was charged with 1500 ml. of 3 Å sieve dried toluene and 340 g. (2.195 moles) of β-isocyanatoethyl methacrylate. With agitation, the mixture was cooled to 5° C. in an ice bath. While maintaining the reaction temperature at 5°–10° C., 39.6 g. ammonia gas was bubbled subsurface over a period of 7 hrs. After the addition was completed, the temperature of the reaction mixture was allowed to rise to 25° C. The precipitated urea product was recovered by filtration, washed with fresh toluene, and dried in a vacuum dessicator to constant weight. Yield was 369 g. (98%). IR analysis (1715 cm$^{-1}$, 1685 cm$^{-1}$, 1600 cm$^{-1}$) and nitrogen analysis (16.3%) were consistent with the mono-substituted urea structure of N-methacryloxyethyl urea.

A one-liter four neck flask equipped with an agitator, thermometer, condenser and pH electrode/meter was charged sequentially with 13 g. distilled water, 95.6 g. of 43.6% aqueous glyoxal solution, 0.25 g. monomethyl ether of hydroquinone, and 125 g. of the above urea. The mixture was agitated until complete solution was achieved. The pH of the mixture was adjusted to 7.0–7.5 with 6.25N NaOH (25% W/V) and the mixture was heated at 60° C. for 5 hr. At the end of this period, analysis for glyoxal indicated 95% reaction. The mixture was diluted with 597 g. distilled water, purified by slurrying with 8.3 g. of a high surface area activated charcoal, and filtered through diatomaceous earth. The active solids content was 20% MEDHEU.

EXAMPLE II

This example describes the preparation of 1-ethyl-3-allyl-4,5-dihydroxy-2-imidazolidinone (EADHEU). The two-step reaction sequence was as follows:

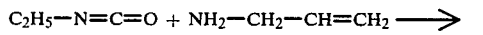

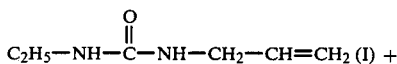

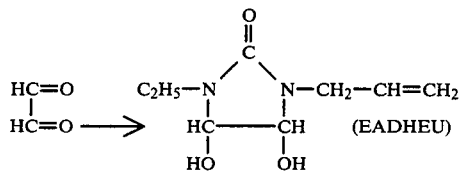

A two-liter reactor equipped with an agitator, thermometer, condenser with drying tube and equalized dropping funnels was charged with 800 ml. of sieve dried toluene and 80 g. allyl amine. With agitation, the mixture was cooled to 10° C. and 100 g. of ethylisocyanate was added over a 2 hr. period. The reaction was exothermic and the temperature was maintained at 10°–15° C. throughout the addition by external cooling. After the addition was completed, the toluene was vacuum distilled from the mixture at 40° C./20 mm. Hg. The viscous liquid was titurated with heptane to precipitate the N-ethyl, N'-allyl-urea. The nitrogen content was 21.3% (21.5% theoretical).

A 500 ml. flask equipped with a thermometer, condenser, and agitator was charged with 75 g. of the above urea, 97.1 g. of 43% aqueous glyoxal, and 87.5 g. distilled water. After complete dissolution of the reactants, the pH was adjusted to 7.0–7.5 with 25% sodium hydroxide and the mixture heated at 80°–85° C. for 4.5 hr. The glyoxal content was monitored during the reaction period. At the end of the heating period, no glyoxal was detected, indicating 100% reaction. The mixture was diluted with water and purified as before. The active solid content was 26.5% EADHEU.

Carbon-13 NMR analysis of the aqueous solution confirmed the presence of the imidazolidinone ring structure. The chemical shifts were as follows:

| Oc ppm | Pattern | Assignment |
| --- | --- | --- |
| 12.9 | Quartet | CH$_2$—$\underline{C}$H$_3$ |
| 35.3 | Triplet | N—$\underline{C}$H$_2$—CH$_3$ |
| 42.5 | Triplet | N—$\underline{C}$H$_2$—CH=CH$_2$ |
| 84.3 | Doublet | $\underline{C}$H(OH) |
| 117.0 | Triplet | $\underline{C}$H=CH$_2$ |
| 132.8 | Doublet | $\underline{C}$H=CH$_2$ |
| 158.8 | Singlet | $\underline{C}$=O |

EXAMPLE III

This example illustrates the preparation of additional imidazolidinone monomers using the procedure of Example II.

Part A

3-Allyl-4,5-dihydroxy-2-imidazolidinone (ADHEU) was prepared using 93.5 g. N-allyl urea, 109 g. 43% aqueous glyoxal, and 60 g. distilled water. The reaction was carried out for 6 hr. at 45°–50° C. Yield was 87%. The active solid content was 43.6%. The monomer had the following structure.

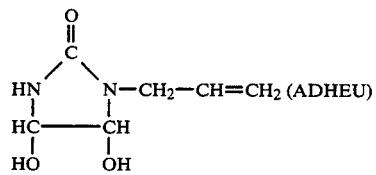

Part B

1-Methyl-3-(methacryloxyethyl)-4,5-dihydroxy-2-imidazolidinone was prepared using 37.2 g. N-methyl-N'-methacryloxyethyl urea, 25.7 g. 43% aqueous glyoxal, and 6 g. water. The reaction was carried out for 6.5 hr. at 60° C. Yield was 94%. The mixture was diluted with 124 g. distilled water. The active solids content was 25%. The monomer had the following structure:

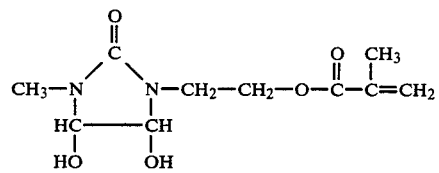

Part C

1-Butyl-3-(2-methyl-1-propenyl)-4,5-dihydroxy-2-imidazolidinone was prepared using 85 g. N-butyl-N'-(2-methyl-1-propenyl) urea, 36.3 g. 80% aqueous glyoxal, and 106 g. water. The reaction was carried out for 8 hr. at 80° C. Yield was 100%. The mixture was diluted with 58 g. distilled water. The active solids content was 39.5%. The monomer had the following structure:

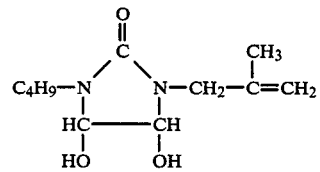

EXAMPLE IV

This example describes the preparation of 3-(β-hydroxyethyl-2-maleoxyethyl)-4,5-dihydroxy-2-imidazolidinone (EMDHEU). The three-step reaction sequence was as follows:

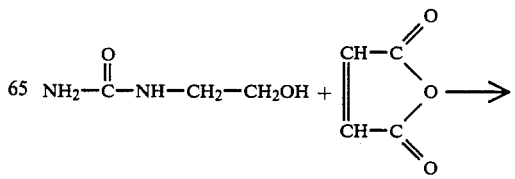

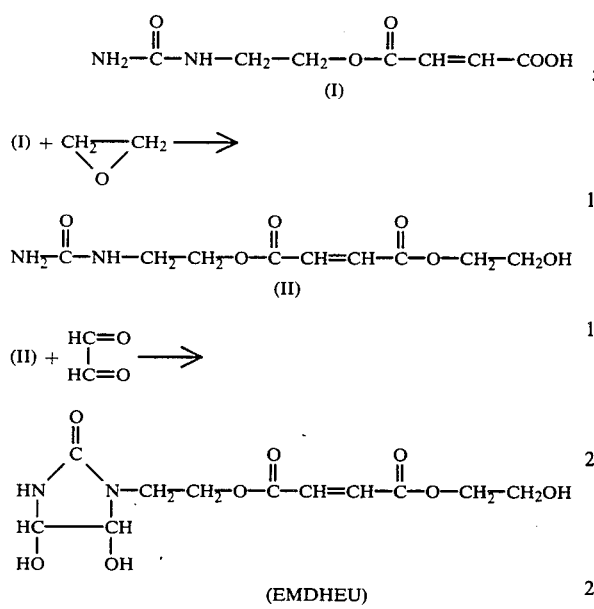

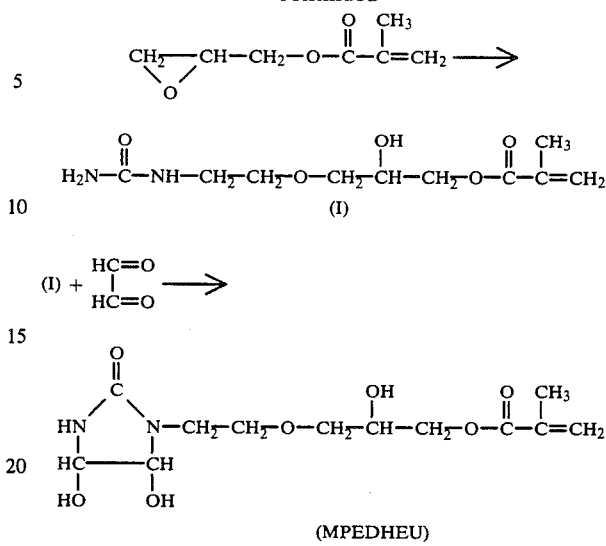

(EMDHEU)

A two-liter round bottom flask, fitted with an agitator, thermometer, condenser, and drying tube, was charged with 1000 ml. of sieve dried toluene, 208 g. (2.0 moles) of β-hydroxyethyl urea and 196 g. (2.0 moles) of maleic anhydride. The reaction mixture was heated to 85°–90° C. Initially the mixture formed two distinct immiscible liquid phases. As the reaction proceeded, the mixture became homogeneous. Heating was continued until infrared analysis showed complete disappearance of the anhydride bands and the acid number of the reaction mixture indicated complete reaction (280 mg. KOH/gm. sample actual vs. 277 theory). The toluene was removed by vacuum stripping. A total of 393.5 g. (97.5% yield) of N-(2-maleoxyethyl) urea was obtained.

While maintaining the above reaction mixture at 80°–85° C., 0.9 g. Na$_2$CO$_3$ was added and the subsurface addition of ethylene oxide (115 g.) was carried out over 6 hours. At the end of the ethylene oxide addition, the acid number was 28 corresponding to a reaction efficiency of 91%. The residual ethylene oxide was removed by a brief vacuum stripping at 80° C. A total of 464 g. of N-(β-hydroxyethyl-2-maleoxyethyl) urea having an acid number of 15 (corresponding to 95% reaction) was obtained.

The above reaction mixture was cooled to 30° C. and 100 g. distilled water and 254 g. of 43% aqueous glyoxal were added. It was adjusted to pH 7.0–7.5 with 25% W/V sodium hydroxide and heated at 60° C. for 2 hr. After this time, no glyoxal was detected in the reaction mixture. It was diluted to 20% solids with 1917 g. water, treated with charcoal and filtered. Yield was 100%.

EXAMPLE V

This example describes the preparation of 3-(methacryloxy-2-hydroxypropoxyethyl)-4,5-dihydroxy-2-imidazolidinone (MPEDHEU). The two-step reaction sequence was as follows:

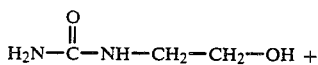

(MPEDHEU)

A 500 ml. round bottom reaction flask fitted with a thermometer, condenser and agitator was charged with 142 g. (1 mole) of glycidyl methacrylate, 0.25 g. monomethyl ether of hydroquinone, 0.75 g. tetramethyl ammonium chloride and 104 g. β-hydroxyethyl urea (1.0 mole). The mixture was heated and stirred at 80°–85° C. until gas-liquid chromatographic (GLC) analysis indicated complete consumption of the glycidyl methacrylate (about 6 hrs.). This is always indicated by testing the water solubility of the reaction mixture. The product is water soluble and near completion of the reaction no turbidity is observed in test samples. The reaction mixture was then cooled to 30° C. and 132 g. of water were added.

A portion of the above reaction mixture containing 154 g. of N-(methacryloxy-2-hydroxypropoxyethyl) urea (0.407 moles) was charged to a 250 ml. reaction vessel equipped with a stirrer, thermometer, and condenser. To this was added 27.7 g. of glyoxal trimer (0.397 mole-83% active) and 7.5 g. distilled water. The pH of the mixture was adjusted to 7.0–7.5 with 25% W/V NaOH and the mixture was heated at 65° C. for 3 hr. The glyoxal content was 0% indicating 100% reaction. The reaction mixture was treated with 4 gms. of activated carbon and filtered. The active solids content was 40%.

EXAMPLE VI

This example describes the preparation of 3-(1-propenoxy-2-hydroxypropoxyethyl)-4,5-dihydroxy-2-imidazolidinone.

The reaction was carried out in a similar manner to that of Example V except that 114 g. allylglycidyl ether (1 mole) was used in place of the glycidyl methacrylate and 135 g. (1 mole) of 43% aqueous glyoxal was used instead of the 83% aqueous glyoxal trimer. The active solids content was 45%. The monomer had the following structure:

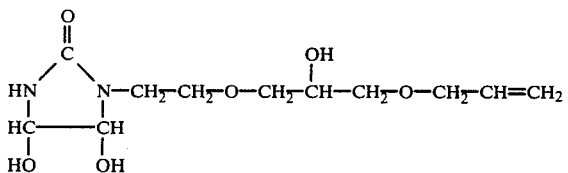

EXAMPLE VII

This example describes the preparation of 3-allyl-4,5-dimethoxy-2-imidazolidinone.

A mixture of 100 g. of N-allyl urea (1 mole), 69.9 g. of 83% glyoxal (1 mole), and 750 g. methanol is stirred for 1 hr. at 35°–40° C. A total of 50 g. of a cation exchange resin (sulfonated polystyrene, H+ form, 5.2 meq./dry g.) is then added. The mixture is stirred for 1 hr. at relux (about 70° C.). The catalyst is removed by filtration, and the reaction mixture is concentrated by vacuum distillation of the solvent. The resulting product should be 232 g. of a syrup at 80% active solids (based on 100% yield). The monomer will have the following structure:

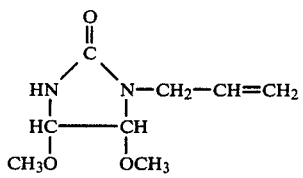

EXAMPLE VIII

This example describes the preparation of 1-ethyl-3-vinyl-4,5-dihydroxy-2-imidazolidinone.

A total of 172 g. of N-vinyl-N'-ethyl urea (1 mole), prepared as described in J. Poly. Science, Part A-1, Vol. 7, 35–46 (1969), is dissolved with stirring in 200 g. distilled water. To this solution is added 69.9 g. 83% glyoxal (1 mole). The pH of the mixture is adjusted to 7.5 with 0.5N NaOH, and the mixture is heated at 70° C. for 4.5 hr. or until a determination of the glyoxal content indicates complete conversion. The mixture is diluted with 133 g. distilled water and 0.23 g. monomethyl ether of hydroquinone. The diluted mixture is treated with 2 g. activated charcoal and filtered. The final product should be an aqueous solution of the monomer at 80% solids (based on 100% yield). The monomer will have the following structure:

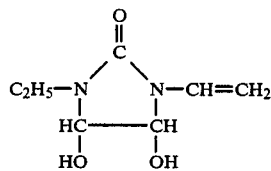

EXAMPLE IX

This example describes the preparation of a surfactant-stabilized latex polymer containing 58.9% vinyl acetate, and 35.3% butyl acrylate, 5.8% of the MED-HEU monomer of Example I. It also describes its evaluation after crosslinking and its use as a binder for nonwoven textiles.

Part A

A two-liter four neck flask was fitted with a thermometer, condenser, agitator, subsurface nitrogen purge, and suitable addition funnels. To the flask was added:
  400 g. distilled water
  2.0 g. 20% sodium dodecyl benzene sulfonate
  2.5 g. 70% ethoxlated nonyl phenol (30 moles EO)
  0.5 g. sodium acetate
  0.8 g. sodium persulfate The mixture was purged subsurface with nitrogen at a rapid rate for 15 min. The gas rate was then reduced, and 50 g. vinyl acetate and 5 g. butyl acrylate were added. Agitation was started.

A monomer pre-emulsion was prepared by combining the following ingredients in a beaker and subjecting the mixture to high speed mixing: 125 g. of the MED-HEU monomer @20%; 10 g. of 30 mole ethoxylated nonyl phenol @70%; 12 g. of 20% sodium dodecyl benzene sulfonate; 200 g. vinyl acetate; 145 g. butyl acrylate. The mixture was transferred to a one-liter dropping funnel. A catalyst solution, designated S-2, was prepared by dissolving 0.7 g. sodium persulfate in 30 g. distilled water.

The initial reactor charge was heated to 72°–75° C. The mixture began to reflux at 72° C. Polymerization was indicated by a change in the mixture's appearance. After the refluxing stopped, the monomer pre-emulsion (S-1) and the catalyst solution (S-2) were slowly added to the reactor over a 4 hr. period at 72°–75° C. After the addition was complete, the batch was held for 1 hr. at 75° C., cooled, and discharged.

The resulting latex had a solids content of 48%. Yield was 98%. The properties of the latex were as follows: a pH of 4.1; intrinisic viscosity of 0.90 dl./g. in dimethyl formamide (DMF); Brookfield viscosity of 175 cps.; particle size of 0.17 nm.; and unfiltered grit (200 mesh) of 40 ppm. No formaldehyde was detected (the detectable limit was 5 ppm).

Part B

In order to evaluate the self-crosslinking capabilities and formaldehyde content of the above latex polymer, films were drawn on polyethylene as uncatalyzed or catalyzed (0.5% oxalic acid on polymer solids) latices. The films were air dried overnight or cured by heating in a forced air draft oven at 130° C. for 5 min. The film specimens were then weighed into enough DMF to make a 1% solution and refluxed for 2 hours. The cooled mixture was filtered, and the amount of soluble polymer was determined by oven solids. A determination of % insolubles was then made. A comparison polymer containing 3% N-methylolacrylamide (NMA), a known self-crosslinking monomer, was also evaluated.

|  | Comparison Latex (containing NMA) | Invention Latex (containing MEDHEU) |
| --- | --- | --- |
| Formaldehyde on latex | 3400 ppm | None |
| Insolubles - air dried | 38% | 45% |
| Insolubles - catalyzed and air dried | 64% | 70% |
| Insolubles - catalyzed and oven cured | 89% | 90% |

The results show the latex containing the self-crosslinking imidazolidinone-containing polymer of the present invention contained no formaldehyde and that it crosslinked as efficiently as the comparison latex containing the self-crosslinking polymer of the prior art.

Part C

The above latex polymers were evaluated as binders for non-woven textiles.

A substrate web of 100% polyester fiber was prepared by carding and subsequently lightly thermally bonded. The latex containing the MEDHEU polymer was formulated wth 1% (dry basic) zinc chloride catalyst. The comparison latex containing the NMA polymer was formulated with 0.5% oxalic acid. The binders were diluted with water to 15% solids. The web was passed through a bath saturated with the binder formulation and squeezed through nip rolls to remove excess binder. Binder add-on was controlled to 40%±4% dry binder, based on fiber weight. This range was equivalent to 26-31% binder on total fabric weight and provided a finished fabric weighing approximately 20 gms./sq. yd. The saturated web was dried on a rotary drum dryer at 120° C. and then cured for 2 min. at 150° C. in a forced air oven. Specimens were tested for wet strength (soaked 5 min. in a 0.5% Aerosol OT solution) and dry strength in the cross machine direction (CD).

| Fabric Treatment | | | Strength | |
|---|---|---|---|---|
| Latex | % Pickup | Basis Wt. | (lbs./linear inch) CD Wet | CD Dry |
| MEDHEU Polymer Latex | 44 | 20.1 | 1.18 | 1.94 |
| NMA Polymer Latex (comparative) | 40 | 20.8 | 1.27 | 1.83 |

The results show that the formaldehyde-free binder containing the self-crosslinking imidozolidinone-containing polymer provided a non-woven textile of comparable wet and dry strength to that prepared using the prior art NMA-containing polymer that self-crosslinks with the release of formaldehyde.

EXAMPLE X

This example describes the preparation of a latex polymer of 82% vinyl acetate, 15% ethylene, and 5% of the EMDHEU monomer of Example IV.

A 1-liter stirred autoclave was charged with 213.5 g. distilled water, 0.011 g. FeSO$_4$, 0.1% in water, 0.057 g. of a 75% solution of sodium dioctyl sulfosuccinate, 1.44 g. of a 80% solution of sodium dihexyl sulfosuccinate, 0.18 g. sodium acetate, and 2.28 g. acetic acid. The reactor was purged and evacuated with nitrogen three times. After purging, 35 g. vinyl acetate was loaded into the reactor. It was pressurized to 500 psi with ethylene and agitation was started.

A monomer pre-emulsion, designated S-1, was prepared by mixing with high speed agitation 85 g. distilled water, 0.5 g. calcium acetate, 5.0 g. partially ethoxylated phosphoric acid, 5.0 g. ethoxylated nonylphenol (40 moles EO), 50.0 g. MPEDHEU monomer at 20% solids, and 245.0 g. vinyl acetate.

Catalyst solutions, designated S-2 and S-3 respectively, were prepared by mixing 1.31 g. sodium persulfate and 17.5 g. distilled water and by mixing 0.52 g. sodium formaldehyde sulfoxylate and 17.5 g. distilled water.

The reactor contents were heated to 40° C. under 500 psi ethylene pressure. At temperature, the monomer pre-emulsion S-1, the oxidant S-2 and the reductant S-3 were added over a 6 hr. period. The reaction temperature was allowed to rise to 70° C. and was maintained at that temperature during the entire polymerization. At the end of the addition, the pressure source was isolated and the reactor pressure was allowed to drop over 2 hr. while maintaining the mixture at 70° C. The reactor was then cooled and the resultant latex discharged.

The latex was 41.1% solids. Conversion was 99%. The latex had the following properties: a pH of 4.2; intrinsic viscosity of 2.44 dl./g. in DMF; Brookfield viscosity of 25 cps.; particle size of 0.19 mm; and grit (200 mesh) of 20 ppm unfiltered. The Tg of the polymer was +3° C.

EXAMPLE XI

Using procedures outlined in Examples IX and X, latex polymers of 48.5% vinyl acetate, 48.5% butyl acrylate, and 3% of the indicated imidazolidinones were prepared. All values are based on 100 parts of the major monomer component and are expressed as active ingredient.

The initial charge was prepared by mixing 76.6 parts distilled water, 0.155 parts of a 31% solution of disodium ethoxylated alcohol half ester of sulfosuccinic acid, 0.42 part of a 70% solution of ethoxylated octyl phenol (30 mole EO), 10 parts vinyl acetate, 1 part butyl acrylate, 0.12 part ammonium persulfate, and 0.04 parts sodium acetate.

The monomer pre-emulsion was prepared from 15.7 parts distilled water, 40 parts vinyl acetate, 49 parts butyl acrylate, 3 parts of the imidazolidinone monomer described hereafter, 0.62 part disodium ethoxylated half ester of sulfosuccinic acid, and 0.7 part of a 70% solution of ethoxylated octyl phenol (30 mole EO). The catalyst used was prepared from 8 parts distilled water and 0.16 part ammonium persulfate.

Latex A prepared using the EADHEU monomer of Example II had a solids content of 48.3%. Conversion was 98%. It had a pH of 3.9; intrinsic viscosity of 1.524 dl./g. in DMF; viscosity of 30 cps.; particle size of 0.25 mm.; and grit (200 mesh) of 60 ppm. unfiltered. The % insolubles uncured (air-dried) and cured were 45 and 90%, respectively.

Latex B prepared using the EMDHEU monomer of Example IV had a solids content of 48.2%. Conversion was 98%. It had a pH of 4.2; intrinsic viscosity of 1.19 dl./g. in DMF; Brookfield viscosity of 77 cps.; particle size of 0.15 mm.; and grit (200 mesh) of 30 ppm. unfiltered. The % insolubles uncured and cured were 11 and 75%, respectively.

EXAMPLE XII

This example describes the preparation of a latex polymer of 87.4% ethyl acrylate, 9.7% methyl methacrylate, and 2.9% of the ADHEU monomer of Example III-Part A. The polymerization procedure previously described was used.

The initial charge was prepared from 71.0 parts distilled water, 0.20 part sodium dodecylbenzene sulfonate, 0.40 part of ethoxylated octyl phenol (30 mole EO), 10 parts ethyl acrylate, and 0.15 part ammonium persulfate. The monomer pre-emulsion was prepared from 13.1 parts distilled water, 80.0 parts ethyl acrylate, 10.0 parts methyl methacrylate, 0.6 part sodium dodecylbenzene sulfonate, and 1.55 parts of ethoxylated octyl phenol (30 mole EO). The self-crosslinking functional monomer solution consisted of 3 parts of the ADHEU monomer and 12.2 parts water. The catalyst solution contained 10 parts water, 0.2 part ammonium persulfate, and 0.1 part sodium bicarbonte.

The resulting latex had a solids content of 47.7%; a pH of 3.2; intrinsic viscosity of 0.603 dl./g. in DMF; Brookfield viscosity of 400 cps.; particle size of 0.17 mm.; and grit (200 mesh) of 10 ppm. The conversion was 95.8%.

EXAMPLE XIII

This example describes the preparation of a polyvinyl alcohol-stabilized latex polymer of about 97.1% vinyl acetate and 2.9% of the MEDHEU monomer of Example I.

A 2-liter reactor was charged with an initial mixture of 288 parts distilled water, 6 parts medium viscosity 88% polyvinyl alcohol, 9 parts high viscosity 88% polyvinyl alcohol, 0.46 parts ammonium persulfate, and 50 parts vinyl acetate. The mixture was heated to reflux (about 72° C.). To the heated mixture were slowly added a pre-emulsion of 90.9 parts distilled water, 0.2 parts medium viscosity 88% polyvinyl alcohol, 75.0 parts of the MEDHEU monomer (20%), 0.45 parts high viscosity 88% polyvinyl alcohol, and 45 parts vinyl acetate and a catalyst solution of 26.5 parts distilled water, 0.75 parts 28% ammonium hydroxide solution, and 0.25 parts ammonium persulfate. The pre-emulsion and catalyst solution were added at a rate sufficient to maintain reflux (over about 3 hr.). After the addition was completed, the batch was cooled and discharged. The resulting latex had a solids content of 52.3%, a pH of 4.6, and Brookfield viscosity of 7000 cps.

Now that the preferred embodiments of the invention have been described in detail, various modifications and improvements thereon will become readily apparent to those skilled in the art. Accordingly, the spirit and scope of the present invention are to be limited only by the appended claims, and not by the foregoing specification.

What is claimed is:

1. A formaldehyde-free polymer emulsion which comprises water and a self-crosslinking imidazolidinone-containing polymer dispersed therein, the polymer comprising about 85–99% of an ethylenically unsaturated monomer and about 1 to 15% by weight of an imidazolidinone monomer having the structure:

$$\begin{array}{c} O \\ \parallel \\ C \\ / \quad \backslash \\ R^1-N \qquad N-X-C(R^2)=CH(R^3), \\ | \qquad\qquad | \\ HC\text{------}CH \\ | \qquad\qquad | \\ R^4O \qquad OR^5 \end{array}$$

wherein $R^1$ is hydrogen or a linear or branched $C_1$–$C_6$ alkyl group; X is a divalent radical selected from the group consisting of $$-(CH_2)_m-, \quad -[CH(R)-CH_2]_n-O-\overset{O}{\underset{\parallel}{C}}-,$$

$$-(CH_2)_n-\overset{R}{\underset{|}{CH}}-O-CH_2-\overset{OH}{\underset{|}{CH}}-CH_2-O-\overset{O}{\underset{\parallel}{C}}, \text{ and}$$

-continued $$-(CH_2)_n-\overset{R}{\underset{|}{CH}}-O-CH_2-\overset{OH}{\underset{|}{CH}}-CH_2-O-CH_2-,$$

with R being hydrogen or a methyl group, m being an integer from 0–5, and n being an integer from 1–5; $R^2$ is hydrogen or a methyl group; $R^3$ is hydrogen or a $$-\overset{O}{\underset{\parallel}{C}}-OR^7$$

group, with $R^7$ being hydrogen or a linear or branched $C_1$–$C_6$ alkyl or hydroxyalkyl group; and $R^4$ and $R^5$ are independently hydrogen or a $C_1$–$C_4$ linear or branched alkyl group.

2. The emulsion of claim 1, wherein the ethylenically unsaturated monomer is ethylene, vinyl acetate, ethyl acrylate, butyl acrylate, methyl methacrylate or mixtures thereof; wherein the imidazolidinone monomer has the structure wherein $R^1$ is hydrogen or a $C_1$–$C_2$ alkyl group; $R^2$ is hydrogen or a methyl group; $R^3$ is hydrogen or $$-\overset{O}{\underset{\parallel}{C}}-O-CH_2-CH_2OH;$$

$R^4$ and $R^5$ are hydrogen; and X is $-CH_2-$ or $$-CH_2-CH_2-O-\overset{O}{\underset{\parallel}{C}}-.$$

3. The emulsion of claim 2, wherein the polymer comprises about 95–97% of the ethylenically unsaturated monomer and about 3–6% of the imidazolidinone monomer.

4. The emulsion of claim 3, wherein the imidazolidinone monomer has the structure wherein $R^1$, $R^3$, $R^4$ and $R^5$ are hydrogen, $R^2$ is a methyl group, and X is $$-CH_2-CH_2-O-\overset{O}{\underset{\parallel}{C}}-;$$

or wherein R' is an ethyl group, $R^2$, $R^3$, $R^4$ and $R^5$ are hydrogen, and X is $-CH_2-$; or wherein $R^1$ $R^2$, $R^3$, $R^4$, and $R^5$ are hydrogen, and X is $-CH_2-$; or wherein $R^1$, $R^2$, $R^4$ and $R^5$ are hydrogen, $$R^3 \text{ is } -\overset{O}{\underset{\parallel}{C}}-O-CH_2-CH_2OH,$$

and X is $$-CH_2-CH_2-O-\overset{O}{\underset{\parallel}{C}}-$$

.

5. The emulsion of claim 1, wherein $R^1$ and $R^7$ are hydrogen or a $C_1$–$C_4$ straight chain alkyl group and $R^2$, $R^4$ and $R^5$ are hydrogen or a methyl group.

6. The emulsion of claim 1, wherein X is $-CH_2-$, $$-CH_2-CH_2-O-\overset{O}{\underset{\parallel}{C}}-,$$

-continued

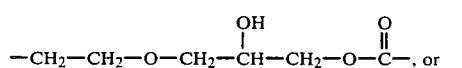

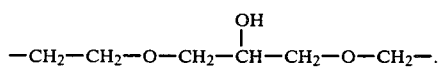

7. The emulsion of claim 1, wherein $R^1$ and $R^7$ are hydrogen or a $C_1$-$C_4$ linear alkyl group; $R^2$ is hydrogen or a methyl group; X is —$(CH_2)_m$—with m being 0 or 1,

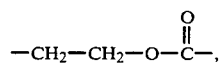

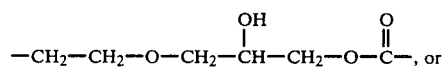

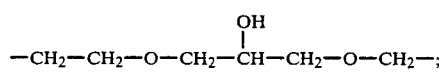

and $R^4$ and $R^5$ are hydrogen or methyl groups.

8. The emulsion of claim 1, wherein $R^1$, $R^3$, $R^4$ and $R^5$ are hydrogen; $R^2$ is a methyl group; and X is

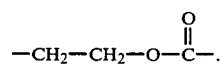

9. The emulsion of claim 1, wherein $R^1$ is an ethyl group; $R^2$, $R^3$, $R^4$ and $R^5$ are hydrogen; and X is —$CH_2$—.

10. The emulsion of claim 1, wherein $R^1$, $R^2$, $R^3$, $R^4$ and $R^5$ are hydrogen and X is —$CH_2$—.

11. The emulsion of claim 1, wherein $R^1$ and $R^2$ are methyl groups; $R^3$, $R^4$ and $R^5$ are hydrogen; and X is

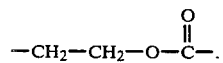

12. The emulsion of claim 1, wherein $R^1$ is a n-butyl group; $R^2$ is a methyl group; $R^3$, $R^4$ and $R^5$ are hydrogen; and X is —$CH_2$—.

13. The emulsion of claim 1, wherein $R^1$, $R^2$, $R^4$ and $R^5$ are hydrogen; $R^3$ is

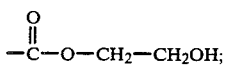

and X is

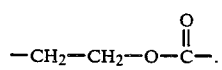

14. The emulsion of claim 1, wherein $R^1$, $R^3$, $R^4$ and $R^5$ are hydrogen; $R^2$ is a methyl group; and X is

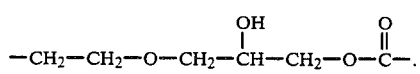

15. The emulsion of claim 1, wherein $R^1$, $R^2$, $R^3$, $R^4$ and $R^5$ are hydrogen and X is

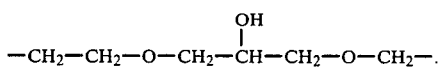

16. The emulsion of claim 1, wherein the ethylenically unsaturated monomer is selected from the group consisting of ethylene, vinyl acetate, ethyl acrylate, butyl acrylate, methyl methacrylate and mixtures thereof.

17. The emulsion of claim 1, wherein the polymer comprises about 45–60% vinyl acetate and about 34–52% butyl acrylate as the ethylenically unsaturated monomer and about 3–6% of the imidazolidinone monomer where $R^1$, $R^3$, $R^4$ and $R^5$ are hydrogen; $R^2$ is methyl; and X is

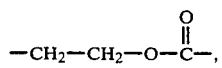

or where $R^1$ is ethyl; $R^2$, $R^3$, $R^4$ and $R^5$ are hydrogen; and X is —$CH_2$—, or where $R^1$, $R^2$, $R^4$ and $R^5$ are hydrogen; $R^3$ is

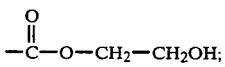

and X is

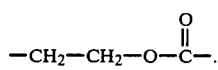

18. The emulsion of claim 1, wherein the polymer comprises about 82% vinyl acetate and about 15% ethylene as the ethylenically unsaturated monomer and about 5% of the imidazolidinone monomer wherein $R^1$, $R^2$, $R^4$ and $R^5$ are H, $R^3$ is

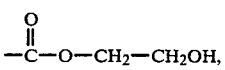

and X is

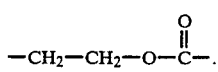

19. The emulsion of claim 1, wherein the polymer comprises about 87% ethyl acrylate and about 10% methyl methacrylate as the ethylenically unsaturated monomer and about 3% of the imidizolidinone monomer wherein $R^1$, $R^2$, $R^3$, $R^4$ and $R^5$ are hydrogen and X is —$CH_2$—.

20. The emulsion of claim 1, wherein the polymer comprises about 97% vinyl acetate as the ethylenically unsaturated monomer and about 3% of the imidazolidonine monomer wherein $R^1$, $R^3$, $R^4$ and $R^5$ are hydrogen, $R^2$ is methyl, and X is

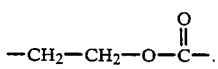

* * * * *